United States Patent [19]
Yuuki et al.

[11] Patent Number: 5,876,722
[45] Date of Patent: *Mar. 2, 1999

[54] DNA ENCODING DERF II, THE MAJOR MITE ALLERGEN, HOST CELLS CONTAINING SUCH DNA AND METHODS FOR PRODUCING DERF II

[75] Inventors: Toshifumi Yuuki; Yasushi Okumura, both of Tokyo; Hiroshi Yamakawa, Urayasu, all of Japan

[73] Assignees: Asahi Breweries, Ltd.; Torii & Co., Ltd., both of Tokyo, Japan

[ * ] Notice: The term of this patent shall not extend beyond the expiration date of Pat. No. 5,798,098.

[21] Appl. No.: 910,075

[22] Filed: Aug. 12, 1997

Related U.S. Application Data

[63] Continuation of Ser. No. 288,888, Aug. 10, 1994, which is a continuation of Ser. No. 658,596, Feb. 21, 1991, abandoned.

[30] Foreign Application Priority Data

Mar. 3, 1990 [JP] Japan ........................................ 2-50848

[51] Int. Cl.$^6$ ........................... A61K 39/35; C12N 15/12; C12N 15/63
[52] U.S. Cl. ..................................... 424/185.1; 424/275.1; 424/276.1; 435/69.3; 435/69.7; 435/252.3; 435/252.33; 435/254.2; 435/255.1; 435/254.11; 435/320.1; 435/325; 435/362; 435/365; 536/23.5
[58] Field of Search ............................... 424/185.1, 275.1, 424/276.1; 435/69.3, 69.7, 252.3, 252.33, 254.2, 255.1, 320.1, 254.11, 325, 362, 365; 536/23.5

[56] References Cited

U.S. PATENT DOCUMENTS

| | | |
|---|---|---|
| 4,837,148 | 6/1989 | Cregg . |
| 4,879,213 | 11/1989 | Fox et al. . |
| 5,433,948 | 7/1995 | Thomas et al. . |
| 5,552,142 | 9/1996 | Thomas et al. . |

FOREIGN PATENT DOCUMENTS

WO88/10297 12/1988 WIPO .

OTHER PUBLICATIONS

Bowie et al, "Deciphering the message in protein sequences: Tolerance to amino acid substitutions", *Science* 247:1306–1310 (1990).

Chua et al, "Sequence analysis of cDNA coding for a major house dust mite allergen, Derp I", *J. Exp. Med.* 167:175–182 (Jan. 1988).

Chua et al, "Isolation of cDNA coding for the major mite allergen Der p II by IgE plaque immunoassay", *Int. Arch. Allergy Appl. Immunol.* 91:118–123 (1990).

Chua et al, "Expression of *Dermatophagoides pteronyssinus* allergen, Der p II, in *Escherichia coli* and the binding studies with human IgE", *Int. Arch. Allergy Appl. Immunol.* 91:124–129 (1990).

Ford et al, "Standardization of *Dermatophagoides pteronyssinus*: Assessment of potency and allergen content in ten coded extracts", *Int. Archs Allergy Appl. Immun.* 76:58–67 (1985).

Greene et al, "Antigenic analysis of group I house dust mite allergens used random fragments of Der p I expressed by recombinant DNA libraries", *Int Arch Allergy Appl Immunol* 92:30–38 (1990).

Haida et al, "Allergens of the house dust mite *Dermatophagoides farinae*—Immunochemical studies of four allerlgenic fractions", *J. Allergy Clin. Immunol.* 75(6):686–692 (Jun. 1985).

Heymann et al, "Antigen Der f I from the dust mite *Dermatophagoides farinae*: Structural comparison with Der p I from *Dermatophagoides pteronyssinus* and epitope specificity of murine IgG and human IgE antibodies", *The Journal of Immunology* 137:2841–2847 (1986).

Ino et al, "Characterization of the proteases in the crude mite extract", *Int Arch Allergy Appl Immunol* 89:321–326 (1989).

Kumar et al, "Amino acid variations at a single residue in an autoimmune peptide profoundly affect its properties: T–cell activation, major histocompatibility complex binding, and ability to block experimental allergic encephalomyelitis", *Proc. Natl. Acad. Sci. USA* 87:1337–1341 (1990).

Maniatis et al, *Molecular Cloning: A Laboratory Manual*, Cold Spring Harbor, 1982, pp. 226–228, 411–413 and 422 (1982).

Stewart et al, "In vitro translation of messenger RNA from the house dust mite *Dermatophagoides pteronyssinus*", *Int. Archs Allergy Appl. Immun.* 83:384–389 (1987).

Suggs et al, "Use of synthetic oligonucleotides as hybridization probes: Isolation of cloned cDNA sequences for human beta2–microglobulin", *Proc. Natl. Acad. Sci. USA* 78(11):6613–6617 (1981).

Thomas et al, "Cloning and expression of DNA coding for the major house dust mite allergen Der p 1 in *Escherichia coli*", *Int. Archs Allergy Appl. Immun.* 85:127–129 (1988).

Thomas et al, "Analysis and expression of cDNA clones coding for house dust mite allergens", *Advances in Biosciences* 74:139–147 (1989).

Tovey et al, "Cloning and sequencing of a cDNA expressing a recombinant house dust mite protein that binds human IgE and corresponds to an important low molecular weight allergen", *J. Exp. Med.* 170:1457–1462 (1989).

Yamashita et al, "Allergens of the house dust mite *Dermatophagoides farinae*. II. Immunological characterization of four allergenic molecules", *Int. Arch Allergy Appl Immunol* 88:173–175 (1988).

(List continued on next page.)

*Primary Examiner*—Anthony C. Caputa
*Attorney, Agent, or Firm*—Browdy and Neimark

[57] ABSTRACT

The invention provides a DNA encoding at least one part of genetic information of protein which has biochemical and immunological properties of a major allergen of *Dermatophagoides farinae* (Derf II).

11 Claims, No Drawings

OTHER PUBLICATIONS

Yasueda et al, "Isolation and characterization of two allergens from *Dermatophagoides farinae*", *Int. Archs Allergy Appl. Immun.* 81:214–223 (1986).

Yasueda et al, "Comparative analysis of physicochemical and immunochemical properties of the two major allergens from *Dermatophagoides pteronyssinus* and the corresponding allergens from *Dermatophagoides farinae*", *Int. Arch Allergy Appl Immunol* 88:402–407 (1989).

Yasueda et al, "Measurement of allergens associated with dust mite allergy", *Int Arch Allergy Appl Immunol* 90:182–189 (1989).

Young et al, "Efficient isolation of genes by using antibody probes", *Proc. Natl. Acad. Sci. USA* 80:1194–1198 (1983).

Yuuki et al, "Cloning and sequencing of cDNAS corresponding to mite major allergen Der f II", *Jpn. J. Allergol.* 39:557–561 (1990).

Chapman et al, Epitope mapping of major dust mite (dermatophagoides) allergens using monoclonal antibodies. In: *Mite Allergy* (Eds. A.L. de Weck, A. Todt), The UCB Institute of Allergy, Brussels, pp. 27–29.

DNA ENCODING DERF II, THE MAJOR MITE ALLERGEN, HOST CELLS CONTAINING SUCH DNA AND METHODS FOR PRODUCING DERF II

CROSS REFERENCE TO RELATED APPLICATIONS

The present application is a continuation of application Ser. No. 08/288,888, filed Aug. 10, 1994, which is a continuation of application Ser. No. 07/658,596, filed Feb. 21, 1991, now abandoned.

BACKGROUND OF THE INVENTION

The present invention relates to DNAs encoding a major allergen of house dust mites, replication vectors, plasmids and host cells which have a concern in the DNAs, and the use thereof.

Allergic diseases generally have several kinds of symptoms which are developed by sensitization of antigen causing the diseases, in which IgE antibody (reagin antibody) specific for allergen in blood serum and tissue is produced, the antibody is exposed again to the antigen and the antibody reacts with the antigen in each tissue.

There is a desensitization therapy as a method for curing drastically the allergic diseases. In the method, the causative antigen is repeatedly administered to a patient in small doses, while the dose is gradually increased according to the symptoms. It is considered that, by the therapy, blocking antibody is produced, the production of the IgE antibody is controlled and the amount of histamine derived from a mast cell is lowered to give treatment effect.

On the other hand, it appears that allergic diseases such as bronchial asthma, childhood asthma, atopic dermatitis and the like are mainly caused by allergy to mites living in house dust. Several kinds of proteins of major mite allergens have been identified (Platts-Mills et al., J. Allergy Clin. Immunol., 80, 755(1987)). The above desensitization therapy of the allergic diseases which uses the major allergens is very effective. However, it is impossible to prepare a large amount of purified allergens which are required in the therapy.

SUMMARY OF THE INVENTION

The inventors of the present invention have found that the above problems are solved by preparing mRNA from *Dermatophagoides farinae* and making a cDNA gene library corresponding to the mRNA, and by isolating a clone expressing Derf II, one of the major allergens, by a colony-immunoassay and isolating DNA fragments containing the objective gene from the clone.

Accordingly, objects of the present invention is to provide a DNA sequence coding the major allergen of mites in genetic engineering and to provide a method for producing a large amount of the objective allergen by expressing and preparing the major mite allergen encoded by the DNA.

The present invention provides a DNA encoding at least one part of genetic information of protein which has biochemical and immunological properties of a major allergen of *Dermatophagoides farinae* (Derf II).

DETAILED DESCRIPTION OF THE INVENTION

To obtain a gene which codes the major mite allergen Derf II, mites are artificially bred with feed or a feed composition for breeding animals such as experimental animals, domestic animals, pet animals and the like, and then the mite bodies can be isolated by a method, for example, a method disclosed in Japanese Patent Unexamined Publication No. 49-69820/1974. To obtain mRNA from the mite bodies, for example, a method disclosed by Chirgwin J. M. et al. is usable (Biochemistry 18, 5294–5299(1979)). Moreover, a commercially available RNA extraction kit (manufactured by Amersham Company, trade name: RPN. 1264) is usable. In general eukaryotic mRNAs having a poly (A) tail at the 3' terminal can be easily purified by an affinity chromatography over oligo (dT) cellulose (Auffray C. et al., Eur. J. Biochem., 107, 303–304(1980)). Further, a commercially available mRNA purification kit (manufactured by Pharmashia Company, trade name: mRNA purification kit 27-9258-01) can be used conveniently.

The mRNA purified is used as a template for synthesizing the first strand of cDNA with reverse transcriptase and primer. Oligo (dT) or synthesized primer may be used. The second strand of cDNA can be synthesized by conventional methods (Huynh, T. V. et al., DNA cloning, Vol. 1, chapter 2, pp49–78(1985), edited by D. M. Glover). A commercially available kit for making cDNA (manufactured by Amersham Company, trade name: RPN. 1256Y) may be also used. The resulting double-stranded cDNA is inserted into a cloning site of a suitable vector, preferably, plasmid pUEX1 (Bressan G. and Stanley K., Nucl. Acids Res., 15, 10056 (1987)). Conventional methods are usable for the insertion of the double-stranded cDNA (Maniatis T. M. et al., Molecular Cloning, Cold Spring Harbor Laboratory, (1982)). The cDNA gene library derived from the mites can express a gene product by transformation of a suitable host, preferably *Escherichia coli*.

Then, a colony which is producing the desired major mite allergen Derf II should be found from the transformed *Escherichia coli*. Although several other methods are usable, colony immunoassay is suitable for that purpose. For example, the following method can be used with pUEX1 as the plasmid.

After the *E. coli* transformed was grown in an L broth agar culture (1% bactotrypton, 0.5% yeast extract, 0.5% sodium chloride, 1.5% bactoagar, 50 μg/ml ampicillin, pH 7.4), the resulting colonies were replicated on a nitrocellulose filter to grow them and recombinant protein was allowed to express on the filter. The cells were lysed by exposure to chloroform vapor and the protein expressed was fixed on the filter.

The inserted DNA derived from the mites bound to the down stream of the DNA encoding β-galactosidase, and the corresponding protein was produced in the form of protein fused together with β-galactosidase. The desired Derf II protein was detected on the filter by using an anti Derf II antibody which was prepared from a rabbit, and two positive clones were obtained. The corresponding *E. coli* colonies were selected from the master agar plate preserved, and they were inoculated to an L broth culture (removing agar from the L broth agar culture). The colonies were cultured with shaking at 30° C. for about 18 hours. The cells were collected from the culture, and plasmids were recovered by a conventional alkali extraction method. The plasmids obtained were digested or not digested. An agarose gel electrophoresis procedure is followed for analyzing DNAs derived from mites which were inserted into the plasmids. About 500 base pairs of DNAs were inserted into the two plasmids pFL1 and pFL11, respectively.

On the other hand, *E. coli* cells were transformed by using the plasmids and vector pUEX1 into which the DNA derived from mites was not inserted, and they were inoculated into the above L broth culture. The cells were cultured with shaking at 30° C. for about three hours and then at 42° C. for about three hours. The resulting cells were collected and washed in a buffer solution (Tris-HCl buffer, 10 mM, pH 7) and fusion protein was extracted by a method of Marston and Carroll et al. (DNA cloning, IRL Press, Volume 3, Chapter 4(1985)). The proteins extracted were subjected to SDS-polyacrylamide gel electrophoresis. Then, the protein separated on the gel was transferred onto a cellulose filter by a Western blot technique (Towbin H. et al., Proc. Natl. Acad. Sci., U.S.A., 76, 4350(1979)). The filter on which the proteins were transferred was blocked with bovine serum albumin, and it was reacted with anti-Derf II antibody which was prepared in a rabbit. Then, the filter was washed with a buffer solution (Tris-HCl buffer: 10 mM, pH 7.4, sodium chloride: 150 mM, Tween 20:0.05%), and it was reacted with anti-rabbit IgG antibody which was labelled with peroxidase (manufactured by Amersham Company). Again, the filter was washed in the same buffer solution and the peroxidase-labelled antibodies remaining without reaction was removed. Further, the filter was reacted with hydrogen peroxide and a dye of 4-chloro-1-naphthol.

As a result, while the band of protein having a molecular weight of about 130 thousands contained in the supernatant which was obtained from the *E. coli* transformed with plasmids pFL1 and pFl11 show positive, no band of protein contained in the supernatant which was obtained from the *E. coli* transformed with the vector without the DNA of ticks show positive. Accordingly, it is apparent that DNA coding Derf II which is a major mite allergen is in the plasmids pFL1 and pFL11, and the gene expresses in *E. coli* as the fused protein together with β-galactosidase.

The DNA segment derived from the mites which is inserted into said plasmids pFL1 and pFL11 can be cleaved with a suitable restriction enzyme, preferably by a complete cleavage with BamHI or partial cleavage with NcoI. The sequences of the cleaved DNA segment can be determined by a dideoxy chain termination method (Sanger F. et al., J. Mol. Biol., 162, 729–773(1982)) and the like. The determined DNA sequences encoding the major mite allergen are shown by Formula I and Formula II. In these Formula I and Formula II, amino acids corresponding to the sequences are shown.

Formula I(SEQ ID NO: 1):

```
  1 GGT ACC ATG GTT TCA TTG TTG GTA GCA GCC  30
  1 Gly Thr Met Val Ser Leu Leu Val Ala Ala  10

31 GTT GTT GCC GAT CAA GTC GAT GTT AAA GAT  60
 11 Val Val Ala Asp Gln Val Asp Val Lys Asp  20

61 TGT GCC AAC AAT GAA ATC AAA AAA GTA ATG  90
 21 (Cys) Ala Asn Asn Glu Ile Lys Lys Val Met  30

91 GTC GAT GGT TGC CAT GGT TCT GAT CCA TGC 120
 31 Val Asp Gly (Cys) His Gly Ser Asp Pro (Cys)  40

121 ATC ATC CAT CGT GGT AAA CCA TTC ACT TTG 150
 41 Ile Ile His Arg Gly Lys Pro Phe Thr Leu  50

151 GAA GCC TTA TTC GAT GCC AAC CAA AAC ACT 180
 51 Glu Ala Leu Phe Asp Ala Asn Gln Asn Thr  60

181 AAA ACC GCT AAA ATT GAA ATC AAA GCC AGC 210
 61 Lys Thr Ala Lys Ile Glu Ile Lys Ala Ser  70

211 CTC GAT GGT CTT GAA ATT GAT GTT CCC GGT 240
 71 Leu Asp Gly Leu Glu Ile Asp Val Pro Gly  80

241 ATC GAT ACC AAT GCT TGC CAT TTT GTC AAA 270
 81 Ile Asp Thr Asn Ala Cys His Phe Val Lys  90

271 TGT CCA TTG GTT AAA GGT CAA CAA TAT GAT 300
 91 Cys Pro Leu Val Lys Gly Gln Gln Tyr Asp 100

301 ATC AAA TAT ACA TGG AAT GTG CCG AAA ATT 330
101 Ile Lys Tyr Thr Trp Asn Val Pro Lys Ile 110

331 GCA CCA AAA TCT GAA AAC GTT GTC GTT ACA 360
111 Ala Pro Lys Ser Glu Asn Val Val Val Thr 120

361 GTC AAA CTT ATC GGT GAT AAT GGT GTT TTG 390
121 Val Lys leu Ile Gly Asp Asn Gly Val Leu 130

391 GCT TGC GCT ATT GCT ACC CAT GGT AAA ATC 420
131 Ala Cys Ala Ile Ala Thr His Gly Lys Ile 140

421 CGT GAT TAA AAA AAA ATA AAT AAG AAA ATT 450
141 Arg Asp ***

451 TTC ACC AAC ATC GAA CAA AAT TCA ATA ACC 480

481 AAA ATT TGA ATC CAA AAA AAA AAA AAA AAA 510

511 ACC ATG G
```

Formula II(SEQ ID NO: 3):

```
  1 GGT ACC ATG GTT TCA TTG TTG GTA GCA GCC  30
  1 Gly Thr Met Val Ser Leu Leu Val Ala Ala  10

31 GTT GTT GCC GAT CAA GTC GAT GTT AAA GAT  60
 11 Val Val Ala Asp Gln Val Asp Val Lys Asp  20

61 TGT GCC AAC AAT GAA ATC AAA AAA GTA ATG  90
 21 (Cys) Ala Asn Asn Glu Ile Lys Lys Val Met  30

91 GTC GAT GGT TGC CAT GGT TCT GAT CCA TGC 120
 31 Val Asp Gly (Cys) His Gly Ser Asp Pro (Cys)  40

121 ATC ATC CAT CGT GGT AAA CCA TTC ACT TTG 150
 41 Ile Ile His Arg Gly Lys Pro Phe Thr Leu  50

151 GAA GCC TTA TTC GAT GCC AAC CAA AAC ACT 180
 51 Glu Ala Leu Phe Asp Ala Asn Gln Asn Thr  60

181 AAA ACC GCT AAA ATT GAA ATC AAA GCC AGC 210
 61 Lys Thr Ala Lys Ile Glu Ile Lys Ala Ser  70

211 CTC GAT GGT CTT GAA ATT GAT GTT CCC GGT 240
 71 Leu Asp Gly Leu Glu Ile Asp Val Pro Gly  80

241 ATC GAT ACC AAT GCT TGC CAT TTT ATG AAA 270
 81 Ile Asp Thr Asn Ala Cys His Phe Met Lys  90

271 TGT CCA TTG GTT AAA GGT CAA CAA TAT GAT 300
 91 Cys Pro Leu Val Lys Gly Gln Gln Tyr Asp 100

301 GCC AAA TAT ACA TGG AAT GTG CCG AAA ATT 330
101 Ala Lys Tyr Thr Trp Asn Val Pro Lys Ile 110

331 GCA CCA AAA TCT GAA AAC GTT GTC GTT ACA 360
111 Ala Pro Lys Ser Glu Asn Val Val Val Thr 120

361 GTC AAA CTT GTT GGT GAT AAT GGT GTT TTG 390
121 Val Lys Leu Val Gly Asp Asn Gly Val Leu 130

391 GCT TGC GCT ATT GCT ACC CAC GCT AAA ATC 420
131 Ala Cys Ala Ile Ala Thr His Ala Lys Ile 140

421 CGT GAT TAA AAA AAA ATA AAT ATG AAA 450
141 Arg Asp ***

451 ATT TTC ACC AAC ATC GAA CAA AAT TCA ATA 480

481 ACC AAA ATT TGA ATC AAA AAA AAA AAA CCA 510

511 TGC
```

Further, the underlined parts in these formulas show the same sequences as those of amino acids shown in the following Table I. *** shows a termination codon.

To confirm the sequences of Formula I and Formula II coding Derf II which is originally the major mite allergen, the Derf II protein was purified, the amino acid sequences were determined, and the sequences were compared with the amino acid sequences shown in Formula I and Formula II. The allergen protein Derf II can be purified by a combination of conventional methods (Biochemical experimental lecture, Vol. 1, "Chemistry of protein", edited by Tamio YAMAKAWA and Kazutomo IMABORI, Tokyo Kagaku Dojin), advantageously by a liquid chromatogrpahic technique. The amino acid sequence of the allergen Derf II purified was determined with a peptide sequencer of Type 471A (manufactured by Applied Biosystem Company). The results are shown in Table I. From these results, it was confirmed that the DNA sequences determined by the above method coded Derf II which was the major mite allergen.

TABLE I

| Analysis No. | Amino acid | Analysis No. | Amino acid | Analysis No. | Amino acid |
|---|---|---|---|---|---|
| 1 | Asp | 16 | Val | 31 | Arg |
| 2 | Gln | 17 | Met | 32 | Gly |
| 3 | Val | 18 | Val | 33 | Lys |
| 4 | Asp | 19 | Asp | 34 | Pro |
| 5 | Val | 20 | Gly | 35 | Phe |
| 6 | Lys | 21 | X | 36 | Thr |
| 7 | Asp | 22 | His | 37 | Leu |
| 8 | X | 23 | Gly | 38 | Glu |
| 9 | Ala | 24 | Ser | 39 | Ala |
| 10 | Asn | 25 | Asp | 40 | Leu |
| 11 | Asn | 26 | Pro | 41 | Phe |
| 12 | Glu | 27 | X | 42 | Asp |
| 13 | Ile | 28 | Ile | 43 | Ala |
| 14 | Lys | 29 | Ile | 44 | Asn |
| 15 | Lys | 30 | His | 45 | Gln |

The DNA segment and a part of the segment can be expressed in yeast with a suitable vector, for example, YEp13 (Broach J. R. et al., Gene, Vol. 8, 121–133(1979)), etc. Suitable yeast cells can be transformed with a yeast vector having an expression casette carrying the mite Derf II gene according to the present invention. For the purpose, the DNA sequences according to the present invention should be placed under controlled conditions of not a E. coli promotor but a strong eukaryotic promotor and the like, for example delta P8 (Otake et al., Agric. Biol. Chem., Vol. 52, 2753–2762(1988)).

The mite Derf II protein prepared by the genetic engineering technique according to the present invention, the fragments of the protein, and the protein fused with the other protein and having biochemical and immunological properties of the major mite allergen Derf II can be used in medical treatment or diagnosis of all sorts of allergic diseases caused by mites.

According to the present invention, a clone which expresses major allergen protein Derf II of *Dermatophagoides farinae* can be isolated by genetic engineering, and DNA fragments containing the desired gene can be isolated from the clone.

As a result, a mass production method of allergen protein can be provided by expressing and by obtaining the major mite allergen which is coded by DNA, and the protein can be used in medical treatment or diagnosis of all sorts of allergic diseases.

Furthermore, DNA hybridizable with and corresponding to the DNA of Formulae I and II and which codes for proteins having the biochemical and immunological properties of Derf II, can be obtained by synthesis, semisynthesis or from nature.

DESCRIPTION OF PREFERRED EMBODIMENTS

The following examples illustrate the present invention in details.

EXAMPLE 1

Construction of a cDNA gene library

Mites were artificially bred for about 30 days in feed for breeding experimental animals under conditions of a temperature of 25° C. and a humidity of 75%. The mites were separated from the feed with a saturated sodium chloride solution, and mites were filtered with suction (Japanese Patent Unexamined Publication No. 49-69820/1974). The mite bodies (wet weight, about 5 g) obtained were rapidly frozen in liquid nitrogen, and then total RNA was extracted and purified with an RNA extraction kit (manufactured by Amersham Company, RPN. 1264). After purifying mRNA from the total RNA with an oligo (dT) column (manufactured by Pharmacia Company, trade name: mRNA purification kit 27-9258-01), about 3 µg of mRNA was obtained. The cDNA was synthesized from the total amount of the mRNA obtained with a cDNA synthesis system plus (manufactured by Amersham Company, trade name: RPN. 1256Y). The RNA extraction, the mRNA purification and the cDNA synthesis followed manuals annexed to the kits.

pUEX1 reported by Bressan et al. (Nucl. Acids Res., Vol. 15, 10056(1987)) was used as an expression vector. By the insertion of a cDNA fragment into the down stream of a β-galactosidase gene, the expression vector could express the desired gene as a fused protein with β-gal. The expression amount was determined by a λ $P_R$ promoter in the upper stream and it was greatly increased by shifting the cultivation temperature to 42° C. The cloning steps follow a method of Haymerle et al. (Nucl. Acids Res., Vol. 14, 8615–8624(1986)) and cDNA cloning system pUEX1 (manufactured by Amersham Company, trade name: RPN. 1282) was used. E. coli MC1061 (gene type: araD139, Δ[ara, leu]7697, ΔlacX74, galU$^-$, galK$^-$, hsr$^-$, hsm$^+$, strA, mcrA$^-$, mcrB$^-$) was used for the transformation. The preparation of competent cells follows a method of Hanahan (DNA cloning, A practical approach, edited by Glover D., IRL Press, Vol. 1, 109(1985)).

EXAMPLE 2

Detection of pFL1 and pFL11

The clones reacting with anti Derf II antibody derived from a rabbit were detected by a colony immunoassay method from the transformants. The transformants were spread on an L broth agar culture plate (1% tryptone manufactured by Difco Company, 0.5% yeast extract manufactured by Difco Company, 0.5% sodium chloride and 1.5% agar) containing 50 µg/ml of ampicillin and these strains were cultured at 30° C. to obtain colonies having a diameter of 1 mm. Nitrocellulose filters (High bond C, manufactured by Amasham Company, trade name: RPN. 1782C) were carefully placed on the colonies to make a replica of the colonies. The remaining colonies on the plate were cultured again at 30° C.

On the other hand, the replica of the colonies blotted onto the nitrocellulose filters was placed on the surface of a new L broth agar plate as the colonies were upside and the colonies were cultured at 42° C. for two hours. Then the nitrocellulose filters were hung in a tank filled with chloroform and exposed to chloroform vapor for about 25 minutes. Each filter having the colonies at the underside was placed on a petri dish. The dish was immersed into 10 ml of TBS buffer (10 mM Tris hydrochloride buffer (pH 7.4) and 150 mM sodium chloride) containing 4 mg of lysozyme and 100

μg of deoxyribonuclease and it was shaken slowly to lyse the colonies for one hour at room temperature. Washing operation was repeated four times by shaking the dish for five minutes with 20 ml of TBS buffer. Then, the filters were immersed into TBS buffer containing 2% bovine serum albumin for one hour as a blocking operation in order to prevent the nonspecific adsorption.

The filters were immersed and shaken for one hour in a solution containing the anti Derf II antibody derived from the rabbit as a primary antibody which was diluted 1000–3000 times with 10 ml of TBS buffer containing 0.2% bovine serum albumin. Then the primary antibody which was not adsorbed was washed away four times with 20 ml of TBST buffer (0.05%, TBS buffer containing Tween 20).

The same procedure as the primary antibody was repeated with filters having a peroxidase-labelled anti rabbit IgG antibody (manufactured by Biorad Company) as a secondary antibody. After adsorbing and washing the antibody, the filters were immersed in TBS buffer in which 0.4 mg/ml of diaminobenzidine as a color-producing reagent was dissolved and hydrogen peroxide water was added in end concentration of 0.01% to obtain colored filters.

The above operation was repeated with about 1600 transformed strains. Two strains of colonies giving a strong signal were found. The corresponding colonies were picked from the master plate and cultured at 30° C. to provide plasmids to be analyzed. The techniques of plasmid extraction, breakage of restriction enzyme, gel electrophoresis and the like were based on a method of Maniatis et al. (Molecular cloning, Cold Spring Harbor Press (1982)). Two kinds of E. coli thus obtained had plasmids into which segments (about 500 base pairs) derived from cDNA were inserted. These were designated as pFL1 and PFL11. These strains were deposited at the National Institute of Bioscience and Human-Technology, Agency of Industrial Science and Technology, 1-3, Higashi 1-chome, Tsukuba-shi, Ibaraki-ken 305, JAPAN, on Dec. 26, 1995, as deposit numbers FERM BP-5356 and FERM BP-5357, respectively.

EXAMPLE 3

Determination of DNA sequence for Derf II gene (pFL1 and pFL11)

The techniques of restriction enzyme treatment of cDNA fragments of pFL1 and pFL11 and ligation thereof and transformation of E. coli host JM105 (gene type: thi, rpsL, endA, sbcB15, hsdR4, Δ(lac-proAB), [F', proAB, lacI$^9$ΔDM15, traD36]) were carried out by conventional methods (Maniatis et al., Molecular Cloning, Cold Spring Harbor Press, p. 104, 146 and 396 (1982); DNA Cloning, IRL Press, Vol. 1, Chapter 6 (1985)). Vectors (pUC118 and pUC119, Messing et al., Methods in Enzymology, Vol. 101, 20–78 (1978)) suitable for Sanger's sequence determination (Science, Vol. 214, 1205–1210 (1985)) was used for the cloning.

Thus isolated Bam HI-cDNA fragments as it was or digested with several restriction enzymes such as Nco I were inserted into vectors which were treated by the same method as described above. The E. coli competent cells were transformed. Each single-stranded DNA of the recombinant plasmids was isolated and purified, and the DNA sequence was determined by the Sanger method. The sequence was analysed by a computer program (DNASIS) manufactured by Hitachi software engineering company.

EXAMPLE 4

Determination of N-terminal amino acid sequence for Derf II protein

Amino acid sequence of Derf II protein purified by reverse phase HPLC was determined. The sequence determination was carried out with a gas phase sequencer manufactured by Applied Biosystems company (Model 471A). Initial amount of 10 μg made it possible to determine the sequence from N-terminal to the 45 amino acid residue. The amino acid sequence obtained was coincident with expected sequence, namely the amino acid sequence estimated from the DNA sequence of cDNA as shown in the above Table I.

EXAMPLE 5

Extraction of fusion proteins and identification of antigenicity

E. coli having pFL1, which were selected from two kinds of E. coli expressing Derf II as fusion proteins and having pFL1 and pFL11 respectively, were cultured in an L broth culture, and the fusion proteins were extracted to confirm their antigenecity. The cells obtained were inoculated in 5 ml of an L broth culture containing 50 μg/ml of ampicillin (L broth-Ap culture) and cultured with shaking at 30° C. overnight. The cultures were inoculated in a 1% L-broth-Ap culture and cultured with shaking at 30° C. When the value of $OD_{660\ nm}$ became 0.6, the same volume of an L-broth-Ap culture which was previously warmed to 54° C. was added. Further they were cultured with shaking for two hours at 42° C. The cells cultured were recovered and extracted by a method of Marston, Carroll et al. (DNA Cloning, IRL Press. Vol. 3, Chapters 4 and 5 (1985)) to obtain fusion proteins. By the observation of a phase-contrast microscope (× 1000), it was confirmed that the fusion proteins were visualised in the cells in the form of inclusion bodies.

The fusion proteins obtained were separated with a SDS-polyacrylamide gel electrophoresis system (manufactured by Daiichi Kagaku company, vertical type, gel concentrations of 4–20%). One part of the cells separated was dyed with Coomassie Brilliant Blue and the other part was transferred on a membrane (manufactured by Imobiron Milipore company) by a Western blot technique (Towbin H. et al., Proc. Natl. Acad. Sci., U.S.A., Vol. 69, 1409–1412 (1972)), and then the expression of Derf II antigen proteins was confirmed with anti Derf II antibodies. Proteins showing positive reaction had a molecular weight of about 130 thousands and they were fused proteins with β-galactosidase.

---

SEQUENCE LISTING ( 1 ) GENERAL INFORMATION:

( i i i ) NUMBER OF SEQUENCES: 4

( 2 ) INFORMATION FOR SEQ ID NO:1:

(i) SEQUENCE CHARACTERISTICS:
  (A) LENGTH: 517 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 1..426

(xi) SEQUENCE DESCRIPTION: SEQ ID NO:1:

| GGT | ACC | ATG | GTT | TCA | TTG | TTG | GTA | GCA | GCC | GTT | GTT | GCC | GAT | CAA | GTC | 48 |
| Gly | Thr | Met | Val | Ser | Leu | Leu | Val | Ala | Ala | Val | Val | Ala | Asp | Gln | Val | |
| 1 | | | | 5 | | | | | 10 | | | | | 15 | | |

| GAT | GTT | AAA | GAT | TGT | GCC | AAC | AAT | GAA | ATC | AAA | AAA | GTA | ATG | GTC | GAT | 96 |
| Asp | Val | Lys | Asp | Cys | Ala | Asn | Asn | Glu | Ile | Lys | Lys | Val | Met | Val | Asp | |
| | | | 20 | | | | | 25 | | | | | 30 | | | |

| GGT | TGC | CAT | GGT | TCT | GAT | CCA | TGC | ATC | ATC | CAT | CGT | GGT | AAA | CCA | TTC | 144 |
| Gly | Cys | His | Gly | Ser | Asp | Pro | Cys | Ile | Ile | His | Arg | Gly | Lys | Pro | Phe | |
| | | 35 | | | | | 40 | | | | | 45 | | | | |

| ACT | TTG | GAA | GCC | TTA | TTC | GAT | GCC | AAC | CAA | AAC | ACT | AAA | ACC | GCT | AAA | 192 |
| Thr | Leu | Glu | Ala | Leu | Phe | Asp | Ala | Asn | Gln | Asn | Thr | Lys | Thr | Ala | Lys | |
| | 50 | | | | | 55 | | | | | 60 | | | | | |

| ATT | GAA | ATC | AAA | GCC | AGC | CTC | GAT | GGT | CTT | GAA | ATT | GAT | GTT | CCC | GGT | 240 |
| Ile | Glu | Ile | Lys | Ala | Ser | Leu | Asp | Gly | Leu | Glu | Ile | Asp | Val | Pro | Gly | |
| 65 | | | | | 70 | | | | | 75 | | | | | 80 | |

| ATC | GAT | ACC | AAT | GCT | TGC | CAT | TTT | GTC | AAA | TGT | CCA | TTG | GTT | AAA | GGT | 288 |
| Ile | Asp | Thr | Asn | Ala | Cys | His | Phe | Val | Lys | Cys | Pro | Leu | Val | Lys | Gly | |
| | | | | 85 | | | | | 90 | | | | | 95 | | |

| CAA | CAA | TAT | GAT | ATC | AAA | TAT | ACA | TGG | AAT | GTG | CCG | AAA | ATT | GCA | CCA | 336 |
| Gln | Gln | Tyr | Asp | Ile | Lys | Tyr | Thr | Trp | Asn | Val | Pro | Lys | Ile | Ala | Pro | |
| | | | 100 | | | | | 105 | | | | | 110 | | | |

| AAA | TCT | GAA | AAC | GTT | GTC | GTT | ACA | GTC | AAA | CTT | ATC | GGT | GAT | AAT | GGT | 384 |
| Lys | Ser | Glu | Asn | Val | Val | Val | Thr | Val | Lys | Leu | Ile | Gly | Asp | Asn | Gly | |
| | | 115 | | | | | 120 | | | | | 125 | | | | |

| GTT | TTG | GCT | TGC | GCT | ATT | GCT | ACC | CAT | GGT | AAA | ATC | CGT | GAT | | | 426 |
| Val | Leu | Ala | Cys | Ala | Ile | Ala | Thr | His | Gly | Lys | Ile | Arg | Asp | | | |
| | 130 | | | | | 135 | | | | | 140 | | | | | |

| TAAAAAAAAA | TAAATAAGAA | AATTTTCACC | AACATCGAAC | AAAATTCAAT | AACCAAAATT | 486 |

| TGAATCCAAA | AAAAAAAAAA | AAAAACCATG | G | | | 517 |

(2) INFORMATION FOR SEQ ID NO:2:

(i) SEQUENCE CHARACTERISTICS:
    (A) LENGTH: 142 amino acids
    (B) TYPE: amino acid
    (D) TOPOLOGY: linear (ii) MOLECULE TYPE: protein (xi) SEQUENCE DESCRIPTION: SEQ ID NO:2:

| Gly | Thr | Met | Val | Ser | Leu | Leu | Val | Ala | Ala | Val | Val | Ala | Asp | Gln | Val |
| 1 | | | | 5 | | | | | 10 | | | | | 15 | |

| Asp | Val | Lys | Asp | Cys | Ala | Asn | Asn | Glu | Ile | Lys | Lys | Val | Met | Val | Asp |
| | | | 20 | | | | | 25 | | | | | 30 | | |

| Gly | Cys | His | Gly | Ser | Asp | Pro | Cys | Ile | Ile | His | Arg | Gly | Lys | Pro | Phe |
| | | 35 | | | | | 40 | | | | | 45 | | | |

| Thr | Leu | Glu | Ala | Leu | Phe | Asp | Ala | Asn | Gln | Asn | Thr | Lys | Thr | Ala | Lys |
| | 50 | | | | | 55 | | | | | 60 | | | | |

| Ile | Glu | Ile | Lys | Ala | Ser | Leu | Asp | Gly | Leu | Glu | Ile | Asp | Val | Pro | Gly |
| 65 | | | | | 70 | | | | | 75 | | | | | 80 |

| Ile | Asp | Thr | Asn | Ala | Cys | His | Phe | Val | Lys | Cys | Pro | Leu | Val | Lys | Gly |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gln | Gln | Tyr | Asp | Ile | Lys | Tyr | Thr | Trp | Asn | Val | Pro | Lys | Ile | Ala | Pro |
|-----|-----|-----|-----|-----|-----|-----|-----|-----|-----|-----|-----|-----|-----|-----|-----|
|     |     |     | 100 |     |     |     | 105 |     |     |     |     | 110 |     |     |     |

| Lys | Ser | Glu | Asn | Val | Val | Val | Thr | Val | Lys | Leu | Ile | Gly | Asp | Asn | Gly |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Val | Leu | Ala | Cys | Ala | Ile | Ala | Thr | His | Gly | Lys | Ile | Arg | Asp |
|-----|-----|-----|-----|-----|-----|-----|-----|-----|-----|-----|-----|-----|-----|
|     | 130 |     |     |     |     | 135 |     |     |     |     | 140 |     |     |

(2) INFORMATION FOR SEQ ID NO:3:

(i) SEQUENCE CHARACTERISTICS:
  (A) LENGTH: 513 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 1..426

(xi) SEQUENCE DESCRIPTION: SEQ ID NO:3:

```
GGT   ACC   ATG   GTT   TCA   TTG   TTG   GTA   GCA   GCC   GTT   GTT   GCC   GAT   CAA   GTC         48
Gly   Thr   Met   Val   Ser   Leu   Leu   Val   Ala   Ala   Val   Val   Ala   Asp   Gln   Val
            145                           150                           155

GAT   GTT   AAA   GAT   TGT   GCC   AAC   AAT   GAA   ATC   AAA   AAA   GTA   ATG   GTC   GAT         96
Asp   Val   Lys   Asp   Cys   Ala   Asn   Asn   Glu   Ile   Lys   Lys   Val   Met   Val   Asp
      160                           165                           170

GGT   TGC   CAT   GGT   TCT   GAT   CCA   TGC   ATC   ATC   CAT   CGT   GGT   AAA   CCA   TTC        144
Gly   Cys   His   Gly   Ser   Asp   Pro   Cys   Ile   Ile   His   Arg   Gly   Lys   Pro   Phe
175                     180                           185                           190

ACT   TTG   GAA   GCC   TTA   TTC   GAT   GCC   AAC   CAA   AAC   ACT   AAA   ACC   GCT   AAA        192
Thr   Leu   Glu   Ala   Leu   Phe   Asp   Ala   Asn   Gln   Asn   Thr   Lys   Thr   Ala   Lys
                        195                           200                           205

ATT   GAA   ATC   AAA   GCC   AGC   CTC   GAT   GGT   CTT   GAA   ATT   GAT   GTT   CCC   GGT        240
Ile   Glu   Ile   Lys   Ala   Ser   Leu   Asp   Gly   Leu   Glu   Ile   Asp   Val   Pro   Gly
                  210                           215                           220

ATC   GAT   ACC   AAT   GCT   TGC   CAT   TTT   ATG   AAA   TGT   CCA   TTG   GTT   AAA   GGT        288
Ile   Asp   Thr   Asn   Ala   Cys   His   Phe   Met   Lys   Cys   Pro   Leu   Val   Lys   Gly
            225                           230                           235

CAA   CAA   TAT   GAT   GCC   AAA   TAT   ACA   TGG   AAT   GTG   CCG   AAA   ATT   GCA   CCA        336
Gln   Gln   Tyr   Asp   Ala   Lys   Tyr   Thr   Trp   Asn   Val   Pro   Lys   Ile   Ala   Pro
      240                           245                           250

AAA   TCT   GAA   AAC   GTT   GTC   GTT   ACA   GTC   AAA   CTT   GTT   GGT   GAT   AAT   GGT        384
Lys   Ser   Glu   Asn   Val   Val   Val   Thr   Val   Lys   Leu   Val   Gly   Asp   Asn   Gly
255                     260                           265                           270

GTT   TTG   GCT   TGC   GCT   ATT   GCT   ACC   CAC   GCT   AAA   ATC   CGT   GAT                    426
Val   Leu   Ala   Cys   Ala   Ile   Ala   Thr   His   Ala   Lys   Ile   Arg   Asp
                        275                           280

TAAAAAAAAA   AAATAAATAT   GAAATTTTC    ACCAACATCG   AACAAAATTC   AATAACCAAA                           486

ATTTGAATCA   AAAAAAAAA    ACCATGC                                                                    513
```

(2) INFORMATION FOR SEQ ID NO:4:

(i) SEQUENCE CHARACTERISTICS:
  (A) LENGTH: 142 amino acids
  (B) TYPE: amino acid
  (D) TOPOLOGY: linear (ii) MOLECULE TYPE: protein (xi) SEQUENCE DESCRIPTION: SEQ ID NO:4:

| Gly<br>1 | Thr | Met | Val | Ser<br>5 | Leu | Leu | Val | Ala | Ala<br>10 | Val | Val | Ala | Asp | Gln<br>15 | Val |
|---|---|---|---|---|---|---|---|---|---|---|---|---|---|---|---|
| Asp | Val | Lys | Asp<br>20 | Cys | Ala | Asn | Asn | Glu<br>25 | Ile | Lys | Lys | Val | Met<br>30 | Val | Asp |
| Gly | Cys | His<br>35 | Gly | Ser | Asp | Pro | Cys<br>40 | Ile | Ile | His | Arg | Gly<br>45 | Lys | Pro | Phe |
| Thr | Leu<br>50 | Glu | Ala | Leu | Phe | Asp<br>55 | Ala | Asn | Gln | Asn | Thr<br>60 | Lys | Thr | Ala | Lys |
| Ile<br>65 | Glu | Ile | Lys | Ala | Ser<br>70 | Leu | Asp | Gly | Leu | Glu<br>75 | Ile | Asp | Val | Pro | Gly<br>80 |
| Ile | Asp | Thr | Asn | Ala<br>85 | Cys | His | Phe | Met | Lys<br>90 | Cys | Pro | Leu | Val | Lys<br>95 | Gly |
| Gln | Gln | Tyr | Asp<br>100 | Ala | Lys | Tyr | Thr | Trp<br>105 | Asn | Val | Pro | Lys | Ile<br>110 | Ala | Pro |
| Lys | Ser | Glu<br>115 | Asn | Val | Val | Val | Thr<br>120 | Val | Lys | Leu | Val | Gly<br>125 | Asp | Asn | Gly |
| Val | Leu<br>130 | Ala | Cys | Ala | Ile | Ala<br>135 | Thr | His | Ala | Lys | Ile<br>140 | Arg | Asp | | |

We claim:

1. An isolated DNA comprising a DNA segment encoding the major mite allergen Derf II of *Dermatophagoides farinae*, wherein said allergen has the amino acid sequence selected from the group consisting of amino acid residues 14–142 of SEQ ID NO: 2 and amino acid residues 14–142 of SEQ ID NO:4.

2. The isolated DNA of claim 1, wherein said DNA segment comprises a nucleic acid sequence selected from the group consisting of nucleotides 40–426 of SEQ ID NO:1 and nucleotides 40–426 of SEQ ID NO:3.

3. A replication vector comprising the nucleic acid sequence of the isolated DNA of claim 1 and at least one selective marker and at least one restriction site outside of said DNA segment.

4. A plasmid comprising the nucleic acid sequence of the isolated DNA of claim 1 and an expression cassette, wherein said cassette comprises said DNA segment.

5. A host cell of a species other than *Dermatophagoides farinae*, comprising the vector of claim 3.

6. The host cell of claim 5, wherein said host cell is a prokaryotic cell.

7. The host cell of claim 6, wherein said prokaryotic cell is *Escherichia coli*.

8. A replication vector comprising the nucleic acid sequence of the isolated DNA of claim 2 and at least one selective marker and at least one restriction site outside of said DNA segment.

9. A method for producing the Derf II allergen, comprising culturing a host cell of a species other than *Dermatophagoides farinae*, wherein said host cell comprises the vector of claim 8, under conditions to permit expression of the Derf II allergen encoded by said DNA segment.

10. In the method for the treatment of an allergic disease by means of desensitization therapy by administering to a subject gradually increasing doses of a causative agent, the improvement wherein said causative agent is the Derf II allergen expressed upon culturing of the host cell of claim 6, under conditions to permit expression of the Derf II allergen encoded by said DNA segment.

11. In the method for the treatment of an allergic disease by means of desensitization therapy by administering to a subject gradually increasing doses of a causative agent, the improvement wherein said causative agent is the Derf II allergen comprising amino acid residues 14–142 of SEQ ID NO:2 or amino acid residues 14–142 of SEQ ID NO:4.

* * * * *